United States Patent
Gruber et al.

(10) Patent No.: US 9,952,227 B2
(45) Date of Patent: Apr. 24, 2018

(54) METHOD FOR DETECTING BILIRUBIN

(71) Applicants: Research Foundation of the City University of New York, New York, NY (US); John B. Pierce Laboratory, New Haven, CT (US)

(72) Inventors: David F. Gruber, Fair Lawn, NJ (US); Jean P. Gaffney, Union, NJ (US); Vincent A. Pieribone, Madison, CT (US)

(73) Assignees: Research Foundation of the City University of New York, New York, NY (US); John B. Pierce Laboratory, New Haven, CT (US)

( * ) Notice: Subject to any disclaimer, the term of this patent is extended or adjusted under 35 U.S.C. 154(b) by 0 days.

(21) Appl. No.: 15/348,563

(22) Filed: Nov. 10, 2016

(65) Prior Publication Data

US 2017/0131296 A1    May 11, 2017

Related U.S. Application Data

(60) Provisional application No. 62/253,291, filed on Nov. 10, 2015.

(51) Int. Cl.
*G01N 21/64* (2006.01)
*G01N 33/72* (2006.01)
*G01N 33/58* (2006.01)

(52) U.S. Cl.
CPC ......... *G01N 33/728* (2013.01); *G01N 33/582* (2013.01); *G01N 2333/43504* (2013.01)

(58) Field of Classification Search
CPC ...................................................... G01N 21/64
See application file for complete search history.

(56) References Cited

U.S. PATENT DOCUMENTS

2016/0009771 A1   1/2016 Miyawaki et al.

OTHER PUBLICATIONS

Kumagai, A. et al.; A Bilirubin-Inducible Fluorescent Protein from Eel Muscle; Cell; Jun, 20, 2013; pp. 1-10; vol. 153; Elsevier Inc.
Park, J. et al.; In Cellulo Mapping of Subcellular Localized Bilirubin; ACS Chemical Biology; May 27, 2016; pp. 2177-2185; vol. 11; American Chemical Society.
Gazzin, S. et al.; A Novel Perspective on the Biology of Bilirubin in Health and Disease; Trends in Molecular Medicine; Sep. 2016; pp. 758-768; vol. 22, No. 9; CellPress.
Gruber, D. et al.; Adaptive Evolution of Eel Fluorescent Proteins from Fatty Acid Binding Proteins Produces Bright Fluorescence in the Marine Environment; PLOS one; Nov. 11, 2015; 99 1-20; DOI:10.1371/journal.pone.0140972; PLOS One.
Murrell, B. et al.; Detecting Individual Sites Subject to Episodic Diversifying Selection; PLOS genetics; Jul. 12, 2012; pp. 1-10; vol. 8, Issue 7; PLOS Genetics.
Hayashi, S. et al.; A novel fluorescent protein purified from eel muscle; The Japanese Society of Fisheries Science; Oct. 17, 2009; pp. 1461-1469; vol. 75; Springer.

*Primary Examiner* — Maryam Monshipouri
(74) *Attorney, Agent, or Firm* — Peter J. Mikesell; Schmeiser, Olsen & Watts, LLP

(57) ABSTRACT

Fluorescent proteins (Chlopsid FP I from *Kaupichthys hyoproroides* and Chlopsid FP II from *Kaupichthys* n. sp.) are used in a method for detecting bilirubin. The proteins are based on transcriptome analysis of the false moray eels, *Kaupichthys hyoproroides* and *Kaupichthys* n. sp., the later representing a heretofore undescribed species.

4 Claims, 2 Drawing Sheets

```
Chlopsid I FP    SEQ ID NO: 1   MFEDFLGTWKCIDSQNFGAYLAAIGAPPVLSERADATRPTVHFN-RDGDK
Chlopsid II FP   SEQ ID NO: 2   MFEDFLGTWECIDSQNFGAYLAAVGAPPVLSDRADATRPTVYFN-RDGDK
Chlopsid I NFP   SEQ ID NO: 3   MVDAFFGTWKLVDSQNFDEYMKALGVGFATRQVGNVTKPTVIIGQ-DGDK Chlopsid I FP    SEQ ID NO: 1   LSLKVEHGPPPLKDVLLSFKLGEEFDEHPTDGRK-CKTLVTFEGDKLLYL
Chlopsid II FP   SEQ ID NO: 2   LSLKVEHGPPPLKDVILSFKLGEEFDEHPTDGRK-CKTLVTFEGDKLLYL
Chlopsid I NFP   SEQ ID NO: 3   VFVKTQS---TFKNTEISFKLGEEFDETTADDRN-CKSVVSMEGNSLVHV Chlopsid I FP    SEQ ID NO: 1   QKWDGKETVVVREIRDGNVVATLSHEGVVALRVYKKVAGPTALE
Chlopsid II FP   SEQ ID NO: 2   QKWDGKETVVVREIRDGNVVATLSHEGVVALRVYKKVAGPTA--
Chlopsid NFP     SEQ ID NO: 3   QKWDGKETKFVREVQDGKLVMKLTFEDVLSVRTYEKA-------
```

METHOD FOR DETECTING BILIRUBIN

CROSS-REFERENCE TO RELATED APPLICATIONS

This application claims priority to and is a non-provisional of U.S. Patent Application 62/253,291 (filed Nov. 10, 2015), the entirety of which is incorporated herein by reference.

STATEMENT OF FEDERALLY SPONSORED RESEARCH OR DEVELOPMENT

This invention was made with government support under grant numbers 1007747, 0444842 and 1257555 awarded by the National Science Foundation and R01NS083875 and U01NS090565-02 awarded by the National Institute of Health. The government has certain rights in the invention.

REFERENCE TO A SEQUENCE LISTING

This application refers to a "Sequence Listing" listed below, which is provided as an electronic document entitled "Sequence.txt" (4 kb created on Nov. 10, 2016) which is incorporated herein by reference in its entirety.

BACKGROUND OF THE INVENTION

The marine environment has proven to be the richest reservoir of novel FPs on the planet. The upper photic ocean is stably monochromatic with downwelling daylight becoming primarily blue (470-490 nm) in color with increasing depth. Over millions of years this stable monochromatic spectral environment likely facilitated the evolution of fluorescent molecules that absorb and re-emit high-energy blue wavelengths into longer, lower energy colors. To date, the two major families of fluorescent molecules with sufficient molar brightness (high cross sections and quantum yield) and expression to produce a fluorescent signal that is visually evident to humans, GFP and the current bilirubin binding proteins discussed here, have evolved exclusively in marine organisms.

The first GFP was discovered in a hydrozoan jellyfish, *Aequorea victoria,* coupled to the bioluminescent apparatus, converting blue bioluminescent light to green. GFP orthologs were later found in non-bioluminescent anthozoas, primarily scleractinian corals. GFP orthologs have also been discovered in a few additional marine organisms including planktonic copepods, lancelets, and a ctenophore. However, it was recently discovered that fluorescence is not only phylogenetically widespread, but is also phenotypically variable across both cartilaginous and bony fishes.

The discussion above is merely provided for general background information and is not intended to be used as an aid in determining the scope of the claimed subject matter.

BRIEF DESCRIPTION OF THE INVENTION

Fluorescent proteins (Chlopsid FP I from *Kaupichthys hyoproroides* and Chlopsid FP II from *Kaupichthys n.* sp.) are used in a method for detecting bilirubin. The proteins are based on transcriptome analysis of the false moray eels, *Kaupichthys hyoproroides* and *Kaupichthys* n. sp., the later representing a heretofore described species.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 1 is sequence alignment showing homology between select peptides; and

DETAILED DESCRIPTION OF THE INVENTION

Figure 2:
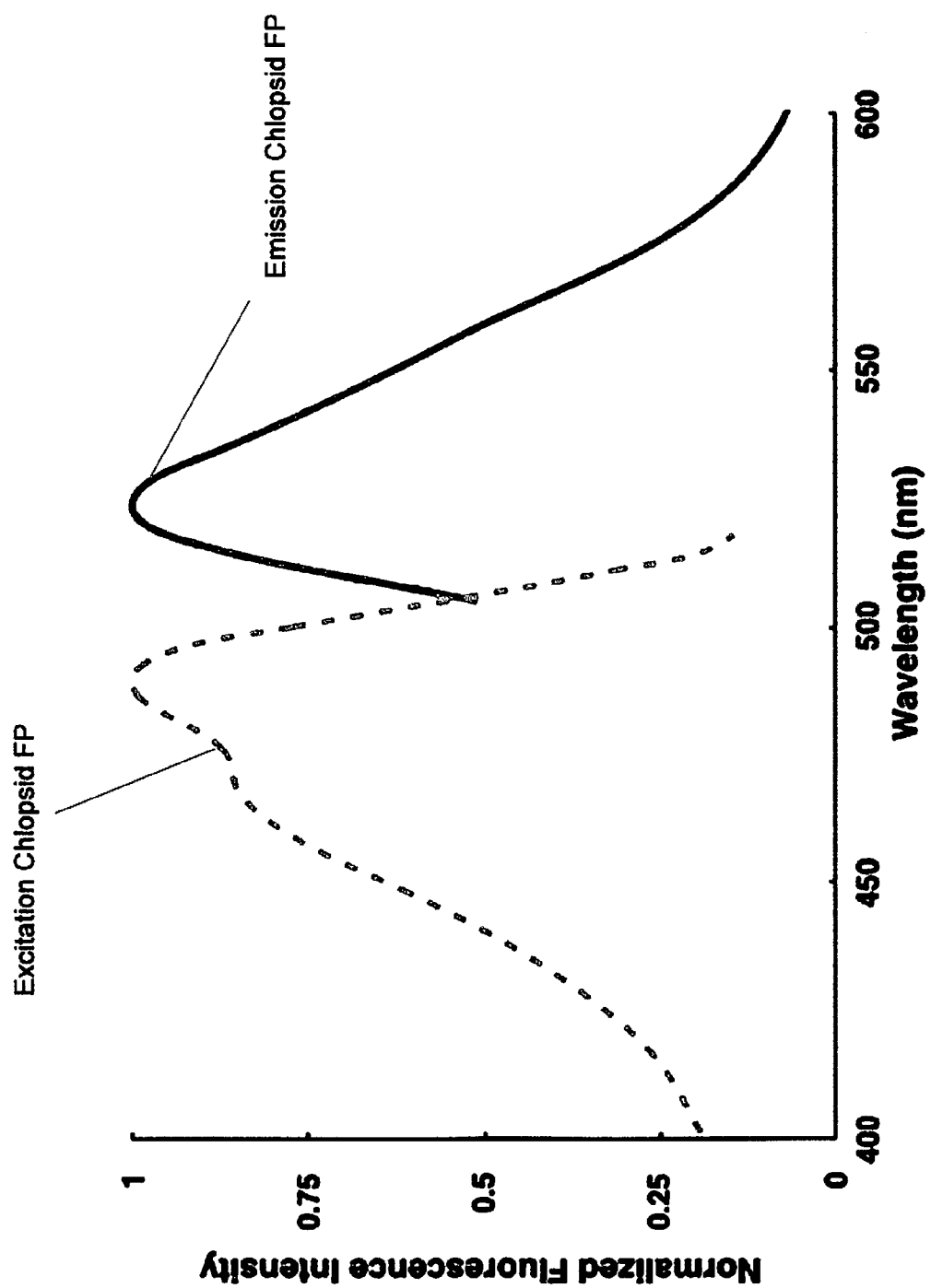
FIG. 2 is a graph showing excitation/emission spectra of Chlopsid FP I.

Disclosed in this specification are two new members of a family of bilirubin-inducible fluorescent proteins (FPs) from marine chlopsid eels and demonstrate a key region of the sequence that serves as an evolutionary switch from non-fluorescent to fluorescent fatty acid-binding proteins (FABPs). Using transcriptomic analysis of two species of brightly fluorescent *Kaupichthys* eels (*Kaupichthys hyoproroides* and *Kaupichthys* n. sp.), two new FPs were identified, cloned and characterized (Chlopsid FP I and Chlopsid FP II). Analogs of these fluorescent proteins are useful in a method for detecting bilirubin. Bilirubin is a degradation product of heme and is therefore an analyte of interest in medical applications (e.g. testing of blood or urine). In one embodiment, quantitative fluorescence is utilized to determine quantify bilirubin concentration. In one embodiment, the fluorescent proteins have a primary structure that is at least 90% homologous with

```
                                    (Chlopsid FPI, SEQ ID NO: 1)
MFEDFLGTWKCIDSQNFGAYLAAIGAPPVLSERADATRPTVHFNRDGDKL

SLKVEHGPPPLKDVLLSFKLGEEFDEHPTDGRKCKTLVTFEGDKLLYLQK

WDGKETVVVREIRDGNVVATLSHEGVVALRVYKKVAGPTALE.
```

In one embodiment, the fluorescent proteins have a primary structure that is at least 90% homologous with (Chlopsid FP II, SEQ ID NO: 2)
MFEDFLGTWECIDSQNFGAYLAAVGAPPVLSDRADATRPTVYFNRDGDKL

SLKVEHGPPPLKDVILSFKLGEEFDEHPTDGRKCKTLVTFEGDKLLYLQK

WDGKETVVVREIRDGNVVATLSHEGVVALRVYKKVAGPTA.

The fluorescent proteins may have a limited number of residues. For example, in one embodiment, there are fewer than 300 residues. In another embodiment, there are fewer than 200 residues. In yet another embodiment, there are fewer than 150 residues.

Phylogenetic analysis was performed on 210 FABPs, spanning 16 vertebrate orders, and including 163 vertebrate taxa. The fluorescent FPs were shown to be diverged as a protein family and are the sister group to brain FABPs. The results indicate that the evolution of this family involved at least three gene duplication events. Fluorescent FABPs were shown to possess a unique, conserved tripeptide Gly-Pro-Pro sequence motif, which is not found in non-fluorescent fatty acid binding proteins. This motif arose from a duplication event of the FABP brain isoforms and was under strong purifying selection, leading to the classification of this new FP family. Residues adjacent to the motif are under strong positive selection, suggesting a further refinement of the eel protein's fluorescent properties. Phylogenetic reconstruction of this emerging FP family is described. Additional fluorescent FABP members are described from groups of distantly related eels. The elucidation of this class of fish FPs with diverse properties provides new templates for the development of protein-based fluorescent tools. The evolutionary adaptation from fatty acid-binding proteins to fluorescent fatty acid-binding proteins raises intrigue as to the functional role of bright green fluorescence in this cryptic genus of reclusive eels that inhabit a blue, nearly monochromatic, marine environment.

Previously, a bilirubin inducible fluorescent protein, UnaG, was identified from *Anguilla japonica*, a species of eel used extensively in aquaculture, and was later fully characterized. Here two new members of this FP family are identified, cloned and characterized and demonstrate that fluorescent FABPs have a unique tri-peptide sequence motif (Gly-Pro-Pro) inserted in a loop between two β sheets, which is not found in other non-fluorescent FABPs. Chlopsid FP I and Chlopsid FP II exhibit blue shifted emission spectra when compared to UnaG. Using analysis of dN/dS skew (MEME option in Datamonkey) this sequence motif is shown to arise from a duplication event of the FABP brain isoforms and was under strong purifying selection during the evolution of the family leading to this new florescent protein family. In addition, residues adjacent to the motif are shown to be under strong positive selection, which may be a further refinement of the fluorescent properties of the proteins in eels. This specification also expands on the identification, biochemical characterization, and phylogentic grouping of this new family of fluorescent eel proteins as first identified by Kumagai et al.

During a January 2011 fluorescent coral reef photomosaic-imaging trip to Bloody Bay Wall off Little Cayman Island in the Caribbean, a green fluorescent chlopsid eel, likely belonging to the genus *Kaupichthys*, was serendipitously photographed. This finding was presented in the American Museum of Natural History exhibit, "*Creatures of Light: Nature's Bioluminescence*" in 2012. The animal seen in the photograph was identified as belonging to the Chlopsidae family of eels, one the most poorly known families of the order Anguilliformes. Chlopsids exhibit extremely cryptic behavior and are rarely seen alive in their natural habitat. Most existing specimens were obtained using piscicides (e.g., rotenone).

Surprised by this animal's bright, visible green fluorescence, we embarked upon a collection expedition to Lee Stocking Island in the Bahamas where we ultimately collected single specimens of two brightly biofluorescent chlopid eel species, *Kaupichthys hyoproroides* and *Kaupichthys* n. sp. *Kaupichthys hyoproroides* reaches a maximum length of about 250 mm and spends most of its life hiding in holes or crevices of coral reef areas or sea grass beds. In cross-section, the fluorescence was found to be bright throughout the muscle tissue and also within the skin in specimens of both species. Muscle tissue was dissected from both species from which we isolated mRNA as well as a highly fluorescent soluble protein extract. The mRNA was used for HiSeq transcriptomic analysis.

Muscle tissue extract from *K. hyoproroides* was subjected to NativeBlue (Invitrogen) non-denaturing gel electrophoresis. Under blue light and imaged with a yellow filter, two bands were observed that exhibited strong green fluorescence. In addition, upon boiling the extract, the fluorescence disappeared. These findings led us to conclude that the fluorescence was most likely arising from a protein. However, transcriptome analysis of the muscle mRNA failed to produce any GFP-like sequences and the fluorescence emission spectrum of the protein extract (not shown) differed from eGFP.

Hayashi and Toda reported that *Anguilla japonica* (heavily farmed in Japanese aquaculture and a historical staple of Japanese cuisine) was weakly green fluorescent. They purified a fluorescent protein from *A. japonica* muscle tissue and isolated and sequenced several peptide fragments. Some of the peptides isolated were found to be homologous to previously published fish fatty acid binding proteins (FABPs). Based on these results, a crude purification was performed of the fluorescent bands from the electrophoresis of eel muscle protein extract and subjected it to mass spectroscopy. The full-length sequences of these proteins in the *Kaupichthys* transcriptome data was identified and synthesized two genes exhibiting the highest homology to the proteins identified by Hayashi and Toda. However, expression of these proteins did not produce visible fluorescence in either *E. coli* or mammalian cells. Then in 2013, Kumagai et al., published a full characterization of the fluorescent protein from *A. japonica*. The protein, termed UnaG, is a novel member of the FABP family, and the fluorophore was found to be a bound bilirubin molecule. Unlike the non-fluorescent FAP sequences synthesized from *Kaupichthys*, the UnaG had an insertion of the tri-peptide Gly-Pro-Pro. The *Kaupichthys hyoproroides* and *Kaupichthys* n. sp. data was re-examined and found a single transcript in each of the two species' transcriptomes that encoded an FABP including the Gly-Pro-Pro insertion. The proteins containing this motif were synthesized and both showed strong green fluorescence in mammalian cells and *E. coli* upon addition of exogenous bilirubin. These proteins, termed Chlopsid FP I and Chlopsid FP II, are orthologs of UnaG (FIG. 1). FIG. 1 depicts sequence alignment of fluorescent FABPs from eels with a non-fluorscent FABP from *Kaupichthys hyoproroides* (Chlopsid NFP) and human brain FABP-7. Areas of homology are identified with solid lines boxes. The GPP sequence motif is identified with a dotted lined box.

Phylogenetic Analysis: The observed phylogenetic patterns indicate that the FABP gene family was generated by at least two duplication events. These duplications possibly coincide with the 1R and 2R duplications in the common ancestor of vertebrates. Alternatively it is possible that a single duplication gave rise to the two major kinds of FABPs and independent duplications in specific fish lineages led to the eel FPs and the Fish Liver-like FABPs. While there is some variation as to the placement of the eel FPs in relation to the liver and brain FABPs depending on the analysis parameters and optimality criteria, the DNA ML analysis and the Bayesian and MP trees place the Eel FPs either sister to or within the brain FABPs. Ther phylogenetic analyses therefore suggest that the eel FPs are more closely related to the brain FABPs than to the liver FABP proteins.

To examine if the neofunctionalization of the FPs as a result of duplications involved sequence specific changes or dN/dS skew, and potentially natural selection, which branches are evolving under different dN/dS skew were observed. Two nodes showed statistically significant difference in skew. The node leading to the brain FABP7 in mammals and birds has a dN/dS ratio of >2.0. The branch leading to the FPs (both *Kaupichthys* and *Anguilla* FPs) has a dN/dS skew >14, indicating strong sequence change in the common ancestor of these eel FPs, similar to what has been reported for opsins.

A site-by-site analysis of dN/dS skew in the FABP7 family of proteins indicates several sites in the protein that show significant skew using the MEME option in Datamonkey under different phylogenetic hypotheses and models of evolution. The number of sites under positive dN/dS skew range from eight (for the NJ tree with the best model) to six (for both of the ML tree analysis regardless of model). It should be noted that there is broad overlap in the inferences made regardless of tree or model of sequence evolution. The Gly-Pro-Pro motif shows strong purifying selection as it is a conserved motif (dN=0; dN/dS=0) in all organisms where it is found. The two amino acids preceding the conserved Gly-Pro-Pro insertion sites in FPs (residue positions 57 and 58) appear to be under strong positive selection. This pattern might suggest that these sites are actively affected by natural selection as a result of the Gly-Pro-Pro insertion in this FP. In addition, there are four sites under positive selection in the carboxy terminus of the protein. Te six sites were observed to have positively skewed dN/dS ratios for altered protein properties we find that the two residues that are adjacent to the Gly-Pro-Pro motif that show dN/dS skew are changing in their refractivity and heat capacity. The other four residues toward the carboxy terminus that show dN/dS skew are changing in their polarity index, their secondary structure factor and in their volume as well as isoelectric point and Refractivity/Heat Capacity.

Properties of fluorescent FABPs: Chlopsid FP I and Chlopsid FP II exhibit a slightly blue-shifted fluorescence excitation and emission spectra compared to UnaG (489 nm/523 nm for UnaG vs 498 nm/527 nm ex/em for Chlopsid FP I and Chlopsid FP II) (FIG. 2). Previous work with UnaG showed that mutation of asparagine-57 to an alanine preceding the GPP motif causes quenching of fluorescence. In Chlopsid FP I and Chlopsid FP II this amino acid is a histidine. This difference in amino acid sequence can potentially explain the fluorescence shift, due to an increase in the π conjugation of the system. This change in fluorescence emission spectra demonstrates that it is possible to make changes to the amino acids around the conjugated bilirubin, which can alter the fluorescence spectrum of the protein.

The fluorescence quantum yield of Chlopsid FP I was determined to be 0.47. Chlopsid FP II had a quantum yield of 0.37. These values are close to the reported quantum yield for UnaG of 0.51 (Table 1). Two prolines in the Gly-Pro-Pro sequence motif were mutated to glycine. This mutation resulted in a decreased quantum yield of 0.11.

TABLE 1

Table of properties for fluorescent proteins

| Fluorescent Protein | Ex/Em maxima (nm) | Fluorescence quantum yield | $O_2$ requirement | Number of amino acids | Molecular weight (kDa) |
|---|---|---|---|---|---|
| Chlopsid FP I | 490/524 | 0.47 | no | 142 | 15.8 |
| Chlopsid FP II | 490/524 | 0.37 | no | 140 | 15.5 |
| Chlopsid FP I-GGG Mutant | 490/524 | 0.11 | no | 142 | 15.3 |
| UnaG | 498/530 | 0.51 | no | 139 | 16.5 |
| EGFP | 490/509 | 0.60 | yes | 238 | 27 |

In the present study, the phylogenetic origins of fluorescent fatty acid binding proteins (FABPs) from marine eels is demonstrated and the key evolutionary motif switch from FABPs to FPs are shown. FABPs are members of the intracellular lipid binding protein family (iLBP) and are involved in reversibly binding and trafficking a wide range of intracellular hydrophobic ligands. FABPs are small (~16 kDa), structurally conserved cytosolic proteins consisting of a interior binding pocket filled with water, surrounded by ten anti-parallel beta sheets forming a beta barrel. At the surface of the beta barrel, two alpha helices cap the pocket and are thought to be involved in regulating ligand binding. In most vertebrates, there are two major kinds of vertebrate FABPs, those found in the brain and those found in the heart. For the fluorescent FABPs, there is a key Gly-Pro-Pro motif that is essential for fluorescence and is present in all fluorescent FABPs. This family of fluorescent eel FABPs is considerably smaller (16 kDa) than GFP (26.9 kDa) (FIG. 1), requires bilirubin for fluorescence, and is oxygen independent.

The order Anguilliformes, the true eels, comprises about 800 species that have traditionally been classified in three major suborders and 111 genera. While *Anguilla* is known to undergo vast migrations (thousands of kilometers) between growth habitats in freshwater and spawning habitats in tropical and subtropical open ocean areas, the poorly studied chlopsid eels are not reported to do so. Therefore, the hypothesis that fluorescence acts as a muscle tissue antioxidant mechanism in *Anguilla*, via the noncovalent binding of bilirubin, may not hold for *Kaupichthys*. In Chlopsidae there is a possibility that fluorescence serves a visual function. During full moon spawning events, the moonlight could potentially stimulate fluorescence and increase species contrast against the blue background of the ocean for these cryptically patterned, and otherwise reclusive fishes. Little visual or reproductive data are available for *Kaupichthys*, however, calculations suggest that these eels exhibit a lunar cycle of reproduction and that they synchronously spawn during or shortly after full moon periods. It is reported for some *Anguilla* species that as they transition during metamorphosis between an adult freshwater yellow eel and the sexually maturing oceanic silver eel, their visual system changes its spectral sensitivity. The middle-wavelength-sensitive cones shifts from ~550 nm to ~525 nm. Fluorescence in coral has been suggested as a means to increase visual contrast in the monochromatic marine environment. Fluorescence appears to play a role in certain visually guided behaviors in reef fishes. In addition, marine fish fluorescence is especially common and morphologically variable in cryptically patterned lineages, providing additional support for the hypothesis that fluorescence serves a visual function for marine organisms. Sexually dimorphic fluorescence patterning has also been observed in some species of marine fishes.

However, it should also be noted however that biofluorescence in eels may be merely a secondary effect of the organism's unusual management of bilirubin as eels are known to manage heme metabolites differently than other vertebrates. For example, unlike all other known vertebrates, the blood plasma of *A. japonica* is blue-green due a high stable concentration of biliverdin. Once produced, biliverdin is further metabolized into bilirubin. However, altered heme metabolite dynamics are not always associated with the emergence of fluoresnceece. For example, lamprey exhibit life cycle dependent bilirubinemia and do not exhibit visible fluorescence, nor do they appear to have a Gly-Pro-Pro containing FABP.

The GFP family has proven to be one of the most useful tools in biomedical science. This current report of the evolutionary consideration of fluorescent fatty acid binding proteins from marine eels that can be autonomously expressed in mammalian cells will expand the toolbox of fluorescent probes available for use in experimental biology. As with GFPs, we find that variations in the primary amino acid sequence of this class of FPs alters the protein's spectral properties. This finding opens the door to mutagenesis investigations that could produce spectral and structural variants (i.e. circular permutants) in which the fluorescence output can be dynamically varied to produce fluorescent event sensors. These findings also raise questions about the behavioral ecology of the poorly known chlopsid eels and if biofluorescence plays a similar functional role (i.e. communication, predator avoidance, prey attraction) as bioluminescence.

Origins and specificity of eel fluorescent FABPs

Chlopsid FP I and Chlopsid FP II are 94% homologous to each other, yet exhibit only 55% sequence homology to UnaG (FIG. 1). One goal was determine how unique the Gly-Pro-Pro sequence is amongst the enormous number of FABPs that have been identified across the animal kingdom. The UnaG, Chlopsid FP I and Chlopsid FP II were used as bait for other vertebrate FABPs. FABP DNA and protein sequences were used for analysis. Phylogenetic trees were generated and it was found that eel FPs from the families Anguillidae and Chlopsidae are either sister to the FABP7 brain clade, which diverged from primitive fishes, or nested within it. Although non-fluorescent FABPs were found in *Kaupichthys* and in the transcriptome of *Anguilla*, these FABPs do not contain the Gly-Pro-Pro tri-peptide motif.

Fluorescent proteins from *Anguilla* and *Kaupichthys* arose from a gene duplication event in these fishes, probably in the common ancestor of the two species. The observed patterns indicate that the larger gene family involved at least three duplication events. Two of these duplications coincide with the 1R and 2R duplications in the common ancestor of vertebrates. The third probably occurred in the common ancestor of eels, and allowed for the neofunctionalization of the duplicated FABP protein into a FP. To examine if the neofunctionalization of the FPs involved sequence specific changes and dN/dS skew, and potentially natural selection, we examined which branches are evolving under different dN/dS skews. Two nodes showed statistically significant difference in skew. The node leading to the brain FABP7 in mammals and birds appears to have a dN/dS ratio of >2.0. The branch leading to the FPs (both *Kaupichthys* and *Anguilla* FPs) has a dN/dS skew >14, indicating strong sequence change in the common ancestor of these eel FPs. The fluorescent eel proteins are, therefore, members of a novel family of FABP7 proteins.

A site-by-site analysis of dN/dS skew in the FABP7 family of proteins indicates several sites in the protein that are showing significant skew using the MEME option in Datamonkey. The Gly-Pro-Pro motif was positively selected for during the evolution of FABPs, leading to the evolution of this new fluorescent protein family. It is interesting to note that this result was inferred using different trees, and while not identical, they are overall very similar. Mapping shows the location of the inserted Gly-Pro-Pro residues in the middle of the eel FPs. There is also significant change in amino acid function very near to the insertion sites in the FPs. While the skewed sites and changed function sites do not directly coincide with the inserts it is interesting to note that regions adjacent to these do exhibit significant patterns. These results suggest that several cluster sites in the protein are showing significant dN/dS ratio. Of these clusters two are adjacent to residues that are responsible for the fluorescent property of these proteins.

Expression in Mammalian Cells: Chlopsid FP I was expressed in mammalian cells (HEK293) without the addition of bilirubin. The cells exhibited bright fluorescence under single and two-photon imaging modalities. The two-photon excitation was fairly flat from 700-1000 nm with a peak at 860 nm and an unusual dip at 840 nm.

Material and Methods:

Fluorescent eel collection and identification: Research, collecting and export permits were obtained from the government of the Bahamas, from the Ministry of Fisheries and Ministry of Environment, Honiara, Solomon Islands, and from the Department of Environment, Cayman Islands. This study was approved and carried out in strict accordance with the recommendations in the Guidelines for the Use of Fishes in Research of the American Fisheries Society and the American Museum of Natural History's Institutional Animal Care and Use Committee (IACUC). Fishes were collected via SCUBA, using both standard open circuit systems and closed circuit rebreathers, via the application of rotenone and quinaldine to a targeted variety of shallow water to deep (mesophotic) habitats in each sampling location where collecting was permitted.

Fluorescent Macro Photography: Both of the chlopsid eel specimens utilized for the transcriptome and protein work described herein (*Kaupichthys hyoproroides* and *Kaupichthys* n. sp.) were immediately placed on ice to preserve coloration and digitally imaged upon return to shore. Prior to imaging, the specimens were subsequently scanned for fluorescence using bright LED light sources equipped with excitation filters and observed using emission filter glasses/goggles. *Kaupichthys hyoproroides* and *Kaupichthys* n. sp. were placed in a narrow photographic tank and held against a thin plate glass front. Fluorescent macro images [4928×3264 (Nikon D7000); 2180×1800 pixel (Nikon D300S)] were produced in a dark room by covering the flash (Nikon SB 600 and SB 800) with band-pass (BP) excitation filters (Omega Optical, Brattleboro, Vt.) and attaching long-pass (LP) (Semrock, Rochester, N.Y.) filters to the front of the camera lens. Two different excitation/emission filter pairs were tested on each sample to stimulate the strongest fluorescence emission: excitation 450-500 nm, emission 514

LP; excitation 500-550 nm, emission 555 and 561 LP. All images were obtained within two hours of collection and the sample was immediately frozen in a liquid nitrogen dry shipper for transport. Cross-sectional images of specimens were generated using a Zeiss-Axio Zoom V16 stereo fluorescent microscope affixed with a Nikon D4 camera.

Fluorescent Protein Isolation from *Kaupichthys* Tissue: A native protein extract was prepared from a small cross-section of eel musculature and was run on a non-denaturing PAGE gel stained with Coomassie Brilliant Blue. Using fluorescent imaging, two bands were observed that exhibited strong green fluorescence.

RNA Extraction and Transcriptome Sequencing: Total RNA was extracted from the caudal musculature of two distinct species of chlopsid eel *K. hyoproroides* and an undescribed species referred to as *Kaupichthys* n. sp. Muscle tissue was homogenized in TriZol reagent (Life Technologies, Carlsbad, Calif.), and the total RNA was precipitated with isopropanol and dissolved in ddH$_2$O. The quality of RNA was assessed on a 2100 Bioanalyzer and with agarose gel electrophoresis. The total RNA was pooled for library preparation using a Hi-seq RNA sample preparation kit (Illumina Inc, San Diego, Calif.) according to the manufacturer's protocol. Sequencing was performed in a multiplexed lane of a flow cell using Illumina Hi-seq 2000. FASTQ file generation was performed by CASAVA ver. 1.8.2 (111umina). Reads were quality checked with FASTQC. Low quality reads and reads containing Illumina adapters were trimmed with Trimmomatic. Reads contaminated with vectors were removed using the NCBI vector database with in-house Perl scripts. Clean reads were uploaded into the NCBI (SRA: SRS493036, Biosample: SAMN02378295).

Trinity was used to generate de novo assembled sequences for downstream analyses (Table 2). Cleaned, assembled contigs have been deposited into the NCBI Transcriptome Shotgun Assembly database under the following accession numbers: PRJNA192511 for *Kaupichthys hyoproroides* and accession PRJNA223153 for *Kaupichthys* n. sp.

TABLE 2

Summary statistics for individual assemblies of Chlopsid I and II

| Assembly | Transcripts >200 bp | N50 (bp) | Mean length (bp) | Max length (bp) | Total number of bases |
|---|---|---|---|---|---|
| TransABySS | | | | | |
| Chlopsid I | 206,683 | 877 | 672.11 | 8,547 | 138,913,931 |
| Trinity | | | | | |
| Chlopsid FP I | 84,610 | 880 | 641 | 13,309 | 54,235,411 |
| Chlopsid FP II | 74,448 | 610 | 502 | 7,558 | 37,356,156 |

N50 = length-weighted median contig length;
bp = base pair;
ORF = Open Reading Frame In Silico Quantification of Transcripts: In order to identify the transcript quality, the reads of *Kaupichthys hyoproroides* were mapped back onto the non-redundant set of assembled transcripts using Bowtie. Gene coverage levels were determined using a Perl script to calculate the RPKM. A total of 109,268,961 (76.67%) reads had at least one reported alignment. The minimum coverage of a transcript was 0.03 FPKM and the maximum was 62,622, with an average of 9.44, indicating a wide range of gene expression (Table 3). Contigs with a RPKM smaller than one were removed for downstream analysis. Among these, 65,877 (77.85%) transcripts had a FPKM >1, with an average of 11.93. Also, two transcripts had FPKMs larger than 20,000, with homology to parvalbumin and muscle related actin, with a FPKM of 24,006 and 62,622, respectively. This level of abundance is expected given that these transcripts were generated from muscle tissue. The EMBOSS package was used to generate all possible open reading frames (ORFs) from stop to stop for each assembled contig.

TABLE 3

Summary statistics of read counts and coverage

| | |
|---|---|
| Total number of reads | 142,526,414 |
| Number of read used reads for assembly | 109,268,961 (76.67%) |
| Number of unused reads | 33,257,453 (23.33%) |
| Number of non-redundant transcripts (>200 bp) | 84,610 |
| Number of transcripts with coverage fpkm >1 | 65,877 |
| Average coverage for contigs with coverage fpkm >1 | 11.93 |
| Average number of reads mapped per contigs | 1,649.71 | bp = base pair
fpkm = paired-reads per-kilo base per million
contig = contiguous overlapping sequence reads Protein Search: The EMBOSS package was used to generate all possible open reading frames (ORFs) from stop to stop for each assembled contig. ORF sequences were searched for FABP using BlastP. Target ORFs with an unusual sequence motif (Gly-Pro-Pro motif) on a loop between two beta sheets in the FABP sequence were selected as potential fluorescent sequences.

Phylogenetic Analysis: Sequences and Tree Construction: The phylogenetic matrix we eventually used has 210 terminals in it. These terminals were obtained using a BLAST search with human FABP7 with an e-value cutoff of e-25. Once we determined that there were two FABP isomers in the majority of the vertebrate taxa with hits at e-25 (one heart isomer and one liver), we then searched the database further for the two paralogs for all of the taxa. This final search resulted in a matrix of 210 terminals over 163 vertebrate species. The DNA sequences were aligned using TranslatorX, which provides both DNA and amino acid sequence alignments that agree at all codons. The DNA sequences were translated into amino acid sequences and these two data sets were formatted into Nexus (for use in PAUP) and Phylip formats (for use in RaxML Blackbox). Maximum likelihood (ML) and maximum parsimony (MP) trees were generated using RaxML blackbox and PAUP. Bootstrap trees for the two methods were also generated. We used Modeltest to determine the best model for the DNA sequence matrix and ProTest for the amino acid sequence matrix. The GAMMA+P-Invar model was used for DNA sequence ML analysis. The WAG with GAMMA+P-Invar model was used for ML analysis of proteins. Bayesian analysis (BY) use 1,000,000 generations with the GAMMA+P-Invar model with default priors (convergence of chains was obtained with this number of generations). In all, ten trees were generated and compared for congruence, where the data source [DNA or Protein] is listed first followed by a slash, then the phylogenetic criterion [MP, ML or BY] listed second followed by a slash, and finally the robustness criterion used [bootstrap or single best tree]). 1) DNA/MP/best tree, 2) DNA/MP/bootstrap, 3) Protein/MP/best tree, 4) DNA/MP/bootstrap; 5) DNA/ML/best tree, 6) DNA/ML/bootstrap, 7) Protein/ML/best tree, 8) Protein/ML/bootstrap; 9) Protein/BY and 10) DNA/BY.

Protein Expression and Purification. Candidate ORFs were selected from eel transcriptome data containing an unusual sequence motif (Gly-Pro-Pro) on a loop between two beta sheets in the FABP sequence. The genes for Chlopsid FP I (*Kaupichthys hyoproroides*) and Chlopsid FP II (*Kaupichthys* n. sp.) were synthesized (GenScript USA) and cloned into the Ndel-Zhol cloning site of a pET-24b(+) vector utilizing the C-terminal His-Tag. Recombinant protein was expressed in a soluble form in BL21(DE3) *E. coli* cells and purified using Ni-affinity chromatography on an AKTA-Prime FPLC, eluting with 50 mM Tris and 300 mM imidazole, pH 8.0. The protein was dialyzed against 50 mM Tris and 20 mM NaCl to remove imidazole, and was concentrated using an Amicon Ultra centrifugal concentrator (m.w.c.o. 3000). Protein purity was confirmed using SDS-PAGE. Protein concentration was determined by $A_{280}$ measurements, using calculated extinction coefficients of 15,300 $M^{-1}$ $cm^{-1}$ for Chlopsid FP I, and 16,600 $M^{-1}$ $cm^{-1}$ for Chlopsid FP II. Bilirubin (Sigma-Aldrich, USA) was dissolved in 0.1 M NaOH and immediately diluted in 50 mM Tris buffer, pH 8.0, for use in experiments.

Fluorescence Spectroscopy: Fluorescence excitation and emission spectra were recorded using a F-7000 Hitachi Fluorescence Spectrometer.

Expression of Chlopsid FP I in HEK293 Cells: A pCS2+ vector was used for cloning of Chlopsid FP I for expression in HEK293 cells (ATCC, USA) using Kpn-Sphl cloning sites. Plasmids were prepared by Genscript USA, Inc. The expression was driven in HEK293 cells (ATCC, USA) by CMV promotor. The HEK293 cell line was maintained in Dulbecco's Modified Eagle Medium (High Glucose) (DMEM) (Invitrogen, USA), supplemented with 10% fetal bovine serum (FBS) (Sigma-Aldrich, USA), in a 37° C. incubator with 5% $CO_2$. Transient transfection was performed using 2 µg of DNA per 35 mm dish and 5 µg of Lipofectamine 2000 (Invitrogen, N.Y.). Cells were imaged on a custom-made 2-photon microscope using a Chameleon Ti-Sapphire laser (Coherent Inc, CA) and water immersion 20×/0.95 N.A. objective (Olympus, Japan). Images were taken using 850 nm laser light with power of 15 mW at the objective.

Analysis of dN/dS ratios: For dN/dS skew detection at the residue level we used the MEME option in Datamonkey and for examining dN/dS skew on branches of the phylogeny (BREL) for these proteins HYPHY was used. The MEME option can use either a NJ tree or a user supplied tree. Hence the MEME option was used with two input trees—the NJ tree and the ML tree obtained by phylogenetic analysis of the data. A model of sequence evolution is also required for MEME and so the default model was used as supplied in Datamonkey and the optimal model as derived from the "automatic model selection tool" option in Datamonkey. The optimal model from Datamonkey automatic model selection tool was 012032. This approach required four separate MEME runs that resulted in from six to eight sites under positive Darwinian selection depending on the parameters of the analysis. The dN/dS branch analysis (BREL) was accomplished with the HYPHY program using the ML tree as an input tree and computing statistics only for internal branches. The PRIME option in Datamonkey was used to characterize the potential change in properties of the residues that experience positive dN/dS skew. PRIME is a variation of MEME that detects residue changes that can be categorized as changes in the original property of the amino acid. There are five categorical changes that can be detected using prime—polarity index, secondary structure factor, volume, refractivity/heat capacity and charge/iso-electric point.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for detecting bilirubin in a subject, the method comprising sequential steps of:
    contacting a polypeptide with a subject, the polypeptide having fluorescent properties in the presence of bilirubin, the polypeptide including a primary structure that is at least 90% homologous with SEQ ID NO: 1 provided residues 57-59 are Gly-Pro-Pro; and
    detecting fluorescence emitted by the polypeptide,
    wherein the subject is a sample derived from blood or urine collected from a living body.

2. The method as recited in claim 1, wherein the primary structure is SEQ ID NO: 1.

3. The method as recited in claim 1, wherein the primary structure is SEQ ID NO: 2.

4. The method as recited in claim 1, wherein the polypeptide has fewer than one hundred fifty residues.

* * * * *

SEQUENCE LISTING

```
<160> NUMBER OF SEQ ID NOS: 3

<210> SEQ ID NO 1
<211> LENGTH: 142
<212> TYPE: PRT
<213> ORGANISM: Kaupichthys hyoproroides

<400> SEQUENCE: 1

Met Phe Glu Asp Phe Leu Gly Thr Trp Lys Cys Ile Asp Ser Gln Asn
1               5                   10                  15

Phe Gly Ala Tyr Leu Ala Ala Ile Gly Ala Pro Pro Val Leu Ser Glu
            20                  25                  30

Arg Ala Asp Ala Thr Arg Pro Thr Val His Phe Asn Arg Asp Gly Asp
        35                  40                  45

Lys Leu Ser Leu Lys Val Glu His Gly Pro Pro Pro Leu Lys Asp Val
    50                  55                  60

Leu Leu Ser Phe Lys Leu Gly Glu Glu Phe Asp Glu His Pro Thr Asp
65                  70                  75                  80

Gly Arg Lys Cys Lys Thr Leu Val Thr Phe Glu Gly Asp Lys Leu Leu
                85                  90                  95

Tyr Leu Gln Lys Trp Asp Gly Lys Glu Thr Val Val Val Arg Glu Ile
```

```
                    100                 105                 110
Arg Asp Gly Asn Val Val Ala Thr Leu Ser His Glu Gly Val Val Ala
                115                 120                 125

Leu Arg Val Tyr Lys Lys Val Ala Gly Pro Thr Ala Leu Glu
            130                 135                 140

<210> SEQ ID NO 2
<211> LENGTH: 140
<212> TYPE: PRT
<213> ORGANISM: Kaupichthys hyoproroides

<400> SEQUENCE: 2

Met Phe Glu Asp Phe Leu Gly Thr Trp Glu Cys Ile Asp Ser Gln Asn
1               5                   10                  15

Phe Gly Ala Tyr Leu Ala Ala Val Gly Ala Pro Pro Val Leu Ser Asp
            20                  25                  30

Arg Ala Asp Ala Thr Arg Pro Thr Val Tyr Phe Asn Arg Asp Gly Asp
        35                  40                  45

Lys Leu Ser Leu Lys Val Glu His Gly Pro Pro Leu Lys Asp Val
    50                  55                  60

Ile Leu Ser Phe Lys Leu Gly Glu Glu Phe Asp Glu His Pro Thr Asp
65              70                  75                  80

Gly Arg Lys Cys Lys Thr Leu Val Thr Phe Glu Gly Asp Lys Leu Leu
                85                  90                  95

Tyr Leu Gln Lys Trp Asp Gly Lys Glu Thr Val Val Arg Glu Ile
            100                 105                 110

Arg Asp Gly Asn Val Val Ala Thr Leu Ser His Glu Gly Val Val Ala
                115                 120                 125

Leu Arg Val Tyr Lys Lys Val Ala Gly Pro Thr Ala
            130                 135                 140

<210> SEQ ID NO 3
<211> LENGTH: 132
<212> TYPE: PRT
<213> ORGANISM: Kaupichthys hyoproroides

<400> SEQUENCE: 3

Met Val Asp Ala Phe Phe Gly Thr Trp Lys Leu Val Asp Ser Gln Asn
1               5                   10                  15

Phe Asp Glu Tyr Met Lys Ala Leu Gly Val Gly Phe Ala Thr Arg Gln
            20                  25                  30

Val Gly Asn Val Thr Lys Pro Thr Val Ile Ile Gly Gln Asp Gly Asp
        35                  40                  45

Lys Val Phe Val Lys Thr Gln Ser Thr Phe Lys Asn Thr Glu Ile Ser
    50                  55                  60

Phe Lys Leu Gly Glu Glu Phe Asp Glu Thr Thr Ala Asp Asp Arg Asn
65              70                  75                  80

Cys Lys Ser Val Val Ser Met Glu Gly Asn Ser Leu Val His Val Gln
                85                  90                  95

Lys Trp Asp Gly Lys Glu Thr Lys Phe Val Arg Glu Val Gln Asp Gly
            100                 105                 110

Lys Leu Val Met Lys Leu Thr Phe Glu Asp Val Leu Ser Val Arg Thr
            115                 120                 125

Tyr Glu Lys Ala
    130
```